United States Patent
Muller et al.

(10) Patent No.: US 6,699,708 B1
(45) Date of Patent: Mar. 2, 2004

(54) PROCESS AND DEVICE FOR TREATING A MIXTURE OF SUBSTANCES CONTAINING ORGANIC MATTER

(76) Inventors: Patrick Muller, Wartenbergstrasse 6, CH-4127 Birsfelden (CH); Christian Widmer, Hoelzlistr 9, 4102 Binningen (CH)

( * ) Notice: Subject to any disclaimer, the term of this patent is extended or adjusted under 35 U.S.C. 154(b) by 0 days.

(21) Appl. No.: 09/830,425
(22) PCT Filed: Nov. 4, 1999
(86) PCT No.: PCT/IB99/01950
§ 371 (c)(1),
(2), (4) Date: May 30, 2001
(87) PCT Pub. No.: WO00/27777
PCT Pub. Date: May 18, 2000

(30) Foreign Application Priority Data

Nov. 6, 1998 (DE) .......................................... 198 51 306
Mar. 3, 1999 (DE) .......................................... 199 09 353

(51) Int. Cl.[7] ................................................ C05F 17/02
(52) U.S. Cl. ............................ 435/262; 435/290.4; 71/9
(58) Field of Search .............................. 435/262, 262.5, 435/264, 266, 290.1, 290.4, 294.1, 300.1; 71/8–10

(56) References Cited

U.S. PATENT DOCUMENTS

| 3,764,290 A | * | 10/1973 | Spohn ............................ 71/9 |
| 4,203,755 A | * | 5/1980 | Ruckstuhl ........................ 71/9 |
| 4,374,804 A | * | 2/1983 | Easter, II ................. 435/290.4 |
| 4,482,633 A | * | 11/1984 | Roediger ................. 435/290.4 |
| 4,758,344 A | * | 7/1988 | Wildenauer ................. 210/603 |
| 4,909,825 A | * | 3/1990 | Eigner ............................. 71/9 |
| 5,066,392 A | | 11/1991 | Kneer |
| 6,281,001 B1 | * | 8/2001 | McNelly ..................... 435/262 |

FOREIGN PATENT DOCUMENTS

| DE | 43 01 116 A1 | 7/1994 | |
| DE | 196 08 586 A1 | 9/1997 | |
| DE | 196 48 731 A1 | 5/1998 | |
| GB | 2273887 A | * 7/1994 | .......... B01D/11/02 |
| JP | 09142980 A | * 6/1997 | ............ C05G/5/00 |
| WO | WO 95/20554 | 8/1995 | |
| WO | WO 97/27158 | 7/1997 | |

* cited by examiner

Primary Examiner—William H. Beisner
(74) Attorney, Agent, or Firm—Oliff & Berridge, PLC (57) ABSTRACT

A process for treating a mixture of substances containing structured constituents and organic matter, and a device for carrying out this process are disclosed. In accordance with the invention, the mixture of substances is subjected to pulse-type or periodical application of force, so that the formation of flow channels for a leaching fluid or process air in a bulk material may be prevented.

20 Claims, 6 Drawing Sheets

PROCESS AND DEVICE FOR TREATING A MIXTURE OF SUBSTANCES CONTAINING ORGANIC MATTER

The invention relates to a process for treating a mixture of substances containing structured constituents and organic matter in accordance with the preamble of claim 1, and a device in particular for carrying out this process.

Such a process is, for example, utilized for treating residual waste matter. In DE 196 48 731 A1 a waste matter treatment method is described, wherein the residual waste matter is treated in a percolator. By such a percolation or extraction, organic constituents, inorganic substances and in a given case water-soluble fatty acids are leached from the waste matter by an extracting or washing agent. The residue is withdrawn from the percolator and, following a subsequent drying, supplied to combustion or dumped.

It was found that by this process the organic substances cannot be removed in the required extent from the residual waste matter.

The drawbacks of this known waste matter treatment process may be eliminated by the process for treating biological waste as disclosed in WO 97/27158 A1. In this process a novel percolator is employed wherein the waste matter passes through the reactor in a horizontal direction (longitudinal direction), and a biogenic reaction is superseded to the percolation process by supplying atmospheric oxygen (process air).

As a result of supplying process air, the cells of the organic matter are split open and the liberated organic substances are carried off by the leaching fluid. In order to avoid channel formation within the waste matter and introduce shear forces, an agitator or circulating apparatus is provided in the reactor, whereby the waste matter is mixed thoroughly in a vertical direction (in parallel with the direction of flow of leaching fluid and process air) and also displaced in the direction of transport.

It is a drawback in this process that for guiding and mixing the waste matter within the reactor, a considerable expense must be incurred which substantially influences the investment costs. Such a complex mechanical structure also harbors the risk of failure of the installation owing to a malfunction in the transport system of the reactor, so that a comparatively high expense for servicing the reactor must be incurred. Such downtimes of the reactor as a result of the necessary maintenance or of a malfunction in the reactor periphery may, however, only be neutralized by providing corresponding buffer spaces wherein intermediate storage of the waste matter during the downtime of the reactor is, possible. In DE 196 08 586 A1 a rotting process is described wherein the exposed pit is subjected to pressured air.

In contrast, the invention is based on the object of furnishing a process for treating a mixture of substances containing structured constituents and organic matter, and a device wherein sufficient decomposition of the organic proportion takes place at minimum expense in terms of device technology.

This object is achieved by the features of claim 1 as far as the process is concerned, and by the features of claim 12 as far as the device is concerned.

Through the measures of causing the mixture of substances (for example residual waste matter) containing structured constituents and organic matter to pass through the reactor in the absence of any substantial longitudinal and transversal mixing, and of preventing channel formation by applying forces to the mixture of substances which are directed approximately in parallel with or transversally to the direction of displacement, the reactor may have a substantially more simple construction than in the above described prior art because it is not necessary to provide an agitator for lateral mixing. The forces are preferably introduced from the peripheral area of the reactor, for example through a suitably designed discharge means or by means of injected gas, preferably pressurized air. In particular when pressurized air is used, shear forces are also applied to the bulk material, whereby the surface of the heap material is reorganized and particles of the mixture of substances are separated into fibers.

The reactor nay be employed as a percolator and dryer without any restructuring or modifications becoming necessary.

Upon introduction of the forces preventing channel formation by way of the discharge means, the mixture of substances is preferably circulated at least in part, so that shear forces are introduced due to the conveyor elements bringing about the circulation.

The flow management according to the invention makes it possible to design the reactor with a high degree of compactness, wherein it is possible to position all of the feeding and discharging means at the head or bottom portion of the reactor.

In a particularly preferred embodiment, the forces for prevention of channel formation and the shear forces required for surface reformation and for tearing open the particles are applied through a pressure gas, preferably pressurized air, which is injected into the bulk material (heap material) from the peripheral area of the reactor. By the pressurized air the heap material is partially expanded, so that a surface reformation takes place in the bulk material and the particles are to=open as a result of the introduced shear forces—the mass transfer area for decomposition of the mixture of substances by means of the atmospheric oxygen and of the leaching fluid is increased.

In a particularly preferred embodiment, the pressurized air and the process air are supplied through nozzles arranged in the foot portion and/or in the bottom portion of the reactor.

In accordance with the invention it is preferred if the mixture of substances passes through the reactor essentially vertically (in parallel with the direction of gravity) or horizontally, so that the mixture of substances is guided approximately in parallel or in a flow transversal to the process air.

In a case where the reactor is employed as a percolator, the leaching fluid is preferably supplied through a distributor in the head portion of the reactor.

The pressurized air is supplied at a pressure of more than 2 bar, preferably more than 4 bar, whereas a pressure of 0.5 bar is customarily applied to the process air.

The nozzles for introduction of the process air and/or pressurized:air may advantageously be controlled individually, so that a specific pressurized air profile may be adjusted across the reactor cross-section.

The use of pressurized air for introducing shear forces and for preventing channel formation has the advantage of the atmospheric oxygen required in the bulk material for the aerobic process being supplied concurrently, so that the pressurized air basically fulfills a twofold function:

1. supplying atmospheric oxygen for aerobic decomposition, and
2. introduction of shear forces.

In a more simple embodiment the forces for preventing channel formation in the bulk material are, for example, supplied through a discharge means arranged at the bottom portion of the reactor. This discharge means may, for example, be a scraper floor installation or a similar conveyor means for discharging the mixture of substances by layers. This variant has the additional advantage of feeding and discharging openings in the bottom portion of the reactor being kept free owing to the advance movement of the discharge means, so that the leaching fluid may exit and pressurized air or process air, respectively, may penetrate into the bulk material. As a discharge means, a worm conveyor carpet, a walking floor, silo filler means etc. may also be used. These discharge means may, of course, also be used in the above described embodiment with pressurized air.

Inasmuch as the mixture of substances passes through the reactor preferably in the form of layers, the dwell time of the mixture of substances inside the reactor may be determined with high precision in the case of continuous process management, so that the passage times with respect to the biological decomposition may be optimized. In the solutions named at the outset, only a mean dwell time value could be determined due to the longitudinal and transversal mixing by means of the agitator.

The laden process air or the laden pressurized air, respectively, are supplied to a waste gas purification wherein organic constituents are separated and the purified air is recycled into the process.

The energy balance of the installation may be further improved if the laden leaching agent is supplied to a sewage water purification. The latter may contain a biogas installation wherein conversion of the organic matter into biogas takes place. Through energetic coupling of the liberated biogas, the process according to the invention may be designed to be largely self-sufficient as regards energy.

In the above described process management, the mixture of substances containing organic matter is subjected to a so-called hydrolysis wherein, through co-operation of air and leaching fluid, the organic material is dissolved and acidified as a result of aerobic, thermophilic heating by the air and carried off by the leaching fluid. I.e., decomposition of the organic constituents takes place as a result of setting a certain humidity and supplying clean air.

Further processing of the mixture of substances provides for drying of the residue in accordance with the invention. Such drying may be effected at minimum energetic expense by aerobic, thermophilic heating of the residue in the reactor. To this end, the mixture of substances may either be subjected to application of clean air in the reactor, so that by the resulting aerobic heating water vapor is discharged via the supplied air; and the residue is dried. Drying and hydrolysis in one single reactor is, however, under the condition of batch-type operation which should be viable only in smaller installations. In larger-sized installations a separate reactor (dryer) is provided for aerobic, thermophilic heating of the residue from hydrolysis. As a matter of fact, these two reactors may also be arranged behind each other in n-fold succession in a single container, so that several hydrolysis/drying steps may follow in succession.

The energy balance of the installation may be further improved if the laden leaching agent of a purification of sewage water is supplied. The latter may contain a biogas installation in which conversion of the organic matter into biogas takes place. Through energetic coupling of the liberated biogas, the process according to the invention may be designed to be self-sufficient as regards energy.

It is quite particularly advantageous if the solid fraction thus treated is supplied to a compacting step following hydrolysis and/or aerobic drying. Here the solid matter presenting a certain particle diameter is pressed into a predetermined geometrical shape, for example pellets or briquets. This compacting step results in further dewatering of the mixture of substances to be treated, so that following compacting a dry-stable body is present which cannot be eluted any further.

This body may, for example, be stored as a substitute fuel being an alternative for fossil energy carriers, or in a garbage dump.

The main application of the process according to the invention presumably resides in the treatment of waste matter; in principle the process may, however, also be applied for any other mixture of substances including organic constituents.

As a washing agent, water is customarily used which is recycled in the process of the invention. The air for hydrolysis and thermophilic drying of the mixture of substances may be guided in counterflow to the mixture of substances but also in parallel flow.

Further advantageous developments of the invention are the subject matters of the further subclaims. In the following, preferred embodiments of the invention are explained in more detail by way of schematic drawings, wherein:

Figure 1:
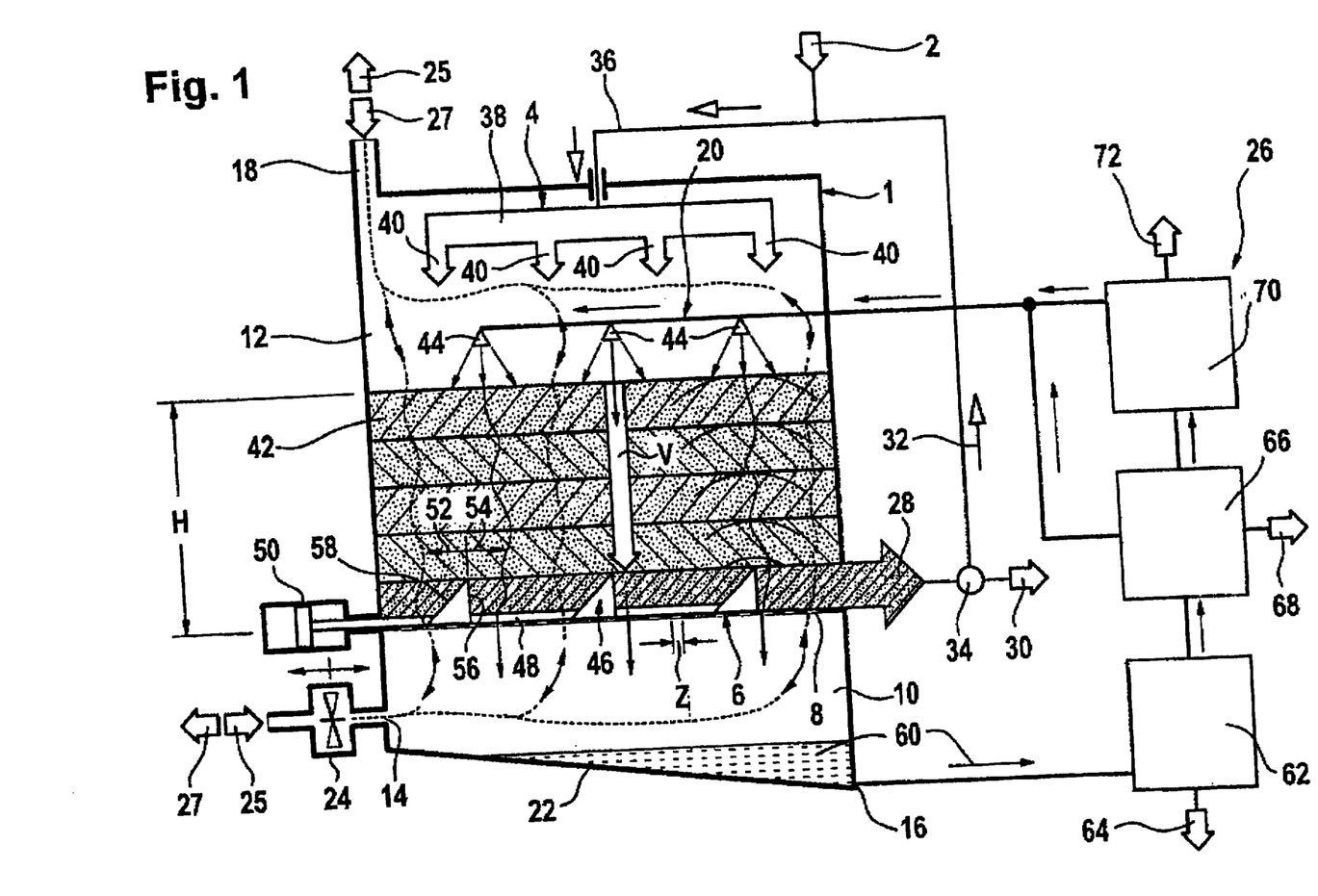
FIG. 1 is a sectional view of a reactor in which hydrolysis of a mixture of substances containing organic constituents takes place.

FIG. 1 shows a process diagram explaining the process of the invention and the device for carrying out the process. Accordingly, the aerobic hydrolysis (aerobic biogenic reaction and percolation) takes place in a reactor 1 to which the mixture of substances 2 to be processed is supplied through a material feeding means 4. The mixture of substances to be processed contains a large proportion of structured material and organic matter. The like mixtures of substances occur, for example, in household waste, biological waste, industrial waste etc.

The reactor 1 is designed as a closed container, so that the material flows described in more detail hereinbelow are supplied via lock means, valve means etc.

The reactor 1 proper preferably is a steel or concrete container that is supplied from above with the mixture of substances (residual waste) in the shown embodiment.

A substantial proportion of the organic fraction of the mixture of substances consists of short-chained compounds that are mostly absorbed on a surface. If this surface is surrounded by a flow of warm water, primarily non-soluble compounds are also hydrolyzed and washed out. The hydrolysis degree depends on the dwelling time in the reactor 1. The smell-intensive components of the mixture of substances and the hydrolysis products are well water-soluble and may be washed out. By percolation one therefore achieves a reduction of the organic matter and a deodorization of the mixture of substances. Together with the leaching fluid (process water), fine sand particles are furthermore carried oft. The reactor 1 is closed so as to be smell tight, and the exhaust air is deodorized in the manner described more closely hereinbelow.

During percolation, process air is additionally supplied, whereby the physico-chemical effect of water extraction is enhanced by intensifying the bacterial decomposition in the aerobic environment, the micro-organisms begin to excrete exoenzymes which split particle-shaped polymer components into monomers and solubilize them.

During percolation, approx. 10% of the inert substances (glass, ceramic, sand) are liberated which are discharged together with the leaching fluid. Separation takes place inside a sand sifter which at the same time allows for supplementary rinsing for sand washing.

In the embodiment in accordance with FIG. 1, the charging means 4 is positioned at the upper end section of the reactor 1 when viewed in the direction of gravity.

In the lower range of the reactor 1 at least one discharge means 6 is formed through which the processed and biologically decomposed mixture of substances may be withdrawn from the reactor 1.

The reactor 1 moreover comprises below the discharge means 6 (representation of FIG. 1) a collector 10 which is separated from a reaction chamber 12 by a sieve floor 8. The discharge means 6, which shall be described in more detail hereinbelow, is designed such that the mixture of substances resting on the sieve floor 8 is discharged from the reactor in a layered configuration, and the openings of the sieve floor 8 are kept unobstructed.

The collector 10 communicates with an air connection duct 14 and a leaching fluid exit 16. In the head area of the reactor 1 another air connection duct 18 and a leaching agent distributor 20 are arranged.

The leaching fluid (water) used for percolation or extraction of the organic constituents of the mixture of substances is fed into the reactor through the distributor 20 and withdrawn through the exit 16. For the purpose of a simplified flow management, the floor 22 of the reactor 1 is inclined towards the exit 16, so that the leaching fluid gathers in the range of the exit 16.

The lower air connection duct 14 in the representation of FIG. 1 is connected with air conveying means 24. Depending on the design of the air conveying means (fan, compressor), a flow 25 from the lower air connection duct 14 to the upper air connection duct La or a flow 27 in a reverse direction from the upper air connection duct 18 to the lower air connection duct 14 may be adjusted inside the reactor 1. I.e., depending on the design of the air conveying means 24, air flows through the mixture of substances received in the reactor 1 from bottom to top or from top to bottom in the representation according to FIG. 1.

The flow of leaching fluid takes place in the direction of gravity, namely, from the distributor 20 disposed in an upper location in the reactor 1 towards the exit 16.

The leaching fluid exiting from the reactor 1 is treated by means of a sewage treatment device 26 (anaerobic filter) described in more detail in the following, and then recirculated to the distributor 20.

The residue resting on the sieve floor 8 is withdrawn as discharge material 28 through the discharge means 6 and either supplied to further processing as a product 30 or, in turn, recycled to the charging means 4 als circulation material 32. The separation of the discharge material 28 into product 30 and/or circulation material 32 takes place through a suitable apportioning means 34 which may, for example, have the form of a slide gate, trap, distributing guide etc.

I.e., by means of suitable adjustment of the apportioning means 34 a part of the discharge material 28 may be recirculated into the reactor 1 als circulation material 32 and may there be utilized for inoculation of the mixture of mubstances and thus for accelerating the biological decomposition.

By circulating all or part of the mixture of substances with the aid of the conveying means, shear forces are moreover introduced into the circulation material, so that surfaces of the mixture of substances are reformed and particles are separated into fibers.

For a better understanding, the above described single components of the device according to the invention shall now be explained in more detail.

The incoming mixture of substances 2 has in advance been treated mechanically in a known manner so as to have a predetermined maximum particle size. This processed mixture of substances 2 is supplied via suitable conveying means, for example conveyor belts 36, to the charging means 4 whereby a distribution of the mixture of substances 2 across the reactor cross-section takes place. In the shown embodiment the charging means 4 includes a transversal conveyor 8 whereby the mixture of substances is distributed in the plane of drawing and in a transversal direction relative to the plane of drawing, and supplied to the reactor 1 by material hoppers 40 which are distributed over the cross-section.

By actuating the material hoppers 40 or the transversal conveyor 38, the mixture of substances 2 is introduced into the reactor 1 in layers, so that practically n-layers 42 are arranged on the sieve floor 8 on top of each other.

The filling height H of the reactor 1 is selected such that the distributor 20 for the leaching fluid is located above the bulk material. The distributor 20 may, for example, present a multiplicity of spraying heads 44 distributed across the reactor cross-section, whereby the leaching fluid may be distributed homogeneously over the topmost layer 42.

In the embodiment represented in FIG. 1, the discharge means 6 has the form of a horizontal conveyor designed such that the respective bottom layer of the mixture of substances resting on the sieve floor 8 may be discharged in a horizontal direction. In the represented reactor 1 the discharge means 6 has the form of a sliding or scraper floor as described, for example, in WO 95/20554 A1. The like sliding floors are, for example, employed in sewage sludge silos, composting installations etc. and are known from the prior art, so that only the essential components shall be described hereinbelow.

In accordance with FIG. 1, the sliding floor includes a plurality of conveyor wedges 46 spaced apart in a horizontal direction (view of FIG. 1) and arranged on a thrust rod 48. The thrust rod 48 may be moved reciprocally, in parallel with arrows 52, 54 in FIG. 1 with the aid of a hydraulic cylinder 50 or some other drive means.

The front surfaces of the conveyor wedges 46 facing the discharge opening have the form of vertical surfaces 56, whereas the rear surfaces are inclined surfaces 58. Through corresponding control of the hydraulic cylinder 50 the thrust rod 48 is periodically moved back and forth, wherein during the movement of the thrust rod 48 in the direction of arrow 52 (to the left in FIG. 1) the mixture of substances of the lowest layer slides upwards along the inclined surface 58 and comes to lie in the space behind the respective conveyor wedge 46. During the subsequent return movement of the thrust rod 48 in the direction of arrow 54, this material is carried along by the vertical surface 56 and conveyed to the right to the neighboring conveyor wedge 46 or to the discharge opening. I.e., the height of the conveyor wedges 46 determines the height of the layers of the discharged mixture of substances. In order to maintain the extracting conditions in the reactor 1 constant, the layer thickness of the discharge material about corresponds to the layer thickness of the material supply, with the filling height H accordingly remaining essentially constant.

As was already mentioned at the outset, a part of the discharge material 28 may be recycled to the conveyor means 36 or directly to the charging means 4 as inoculation material (circulation material 32). In principle it is also possible to use all of the discharge material 28 als circulation material 32, in which case the mixture of substances passes through the reactor 1 several times and is only discharged as product 30 following, for example, 4 runs.

The sieve floor 8 arranged underneath the discharge means 6 has a mesh size Z selected as a function of the composition and particle size of the mixture of substances to be processed. The construction of the thrust rod 48 and of the conveyor wedges 46 is selected such that the sieve floor 8 is cleaned by the reciprocating movement of the scraper floor, so that an obstruction of the meshes may be prevented.

Layered discharge of material results in a movement of layers of the mixture of substances from top to bottom through the reactor 1 in a vertical direction (FIG. 1).

As was already mentioned above, the air conveying means 24 may have the form of a fan or compressor, 80 that different directions of air flow may be adjusted in the reactor 1. In either case the entry and exit ranges of the reactor 1 are selected such that the air flows through the layered mixture of substances while being distributed over the entire reactor cross-section. This air flow is indicated by dashed lines in the representation of FIG. 1.

The leaching fluid flows through the layered mixture of substances along the solid-line arrows from top to bottom and enters, laden with organic matter, into the collector 10 through the sieve floor 8. The laden leaching fluid 60 is withdrawn via the exit 16 and supplied to the sewage treatment device 26. The latter comprises a foreign matter separator 62 in which foreign matter 64 such as, for example, sand, pebbles, suspended matter, float matter etc. are separated out. Such foreign matter separators may, for example, comprise a settling tank and a skimmer for separating out the mentioned foreign matter 64.

The leaching fluid freed from the foreign matter and containing colloidal organic compounds in aqueous phase is then supplied to an anaerobic fermeter 66, for example a biogas or digestion tower installation. Metabolic end products produced in this anaerobic waste water treatment are methane and carbon dioxide and in some cases small amounts of hydrogen sulfide. This biogas obtained as a decomposition product may be converted into electricity and heat in suitable block-type thermal power stations. A part of the energy recovered from the biogas is returned into the process of the invention which is thus largely self-sufficient as regards energy.

Preliminary trials showed that in the treatment of one [metric] ton of supplied household waste, approx. 80 Nm$^3$ of biogas having an energy content of 6.5 kWh may be obtained.

In the above described embodiment a sewage water purification plant is associated with the reactor. As an alternative, the leaching fluid might also be incorporated into an existing sewage purification plant, or be introduced directly into the sewers, or supplied to another treatment step. For the supply, fresh water or industrial process water or weakly loaded sewage water will be used in that case.

The anaerobic fermenter 66 is followed immediately by a two-stage aerobic after treatment 70, wherein digestion process water from the biogas installation is subjected to an after treatment for minimizing the residual load, and nitrogen is eliminated.

Depending on load and legal regulations in force, the loaded sewage 72 thereby produced is supplied to a further treatment stage or directly introduced into the sewer system. The leaching fluid purified in the aerobic biological stage 70 is then supplied to the reactor 1 by way of the distributor 20. As is indicated in FIG. 1, a partial flow of the digestion process water may be supplied directly from the anaerobic fermenter 66 to the distributor while bypassing the 2-stage aerobic biological stage 70, in order to exert a catalytic influence on biological decomposition in the reactor 1.

As a result of the flow management according to the invention inside the reactor 1, aerobic hydrolysis takes place, with an aerobic, thermophilic heating occurring as a result of the air flowing through the mixture of substances 2 and the humidity of the mixture of substances which is adjusted by way of the leaching fluid, whereby the cells of the organic matter are split open and the liberated organic substances are discharged by the leaching fluid.

Decomposition of the organic materials is due, on the one hand, to the aerobic decomposition of the available carbon C into $CO_2$ (carbonic acid) and on the other hand to leaching out of the dissolved and acidified organic matter and removal by way of the leaching fluid. Due to the aerobic, thermophilic reaction and the simultaneous decomposition of the organic compounds, the temperature in the mixture of substances rises (to approx. 40 to 50° C., for example) during the extracting step. As a result of this temperature increase water vapor is liberated, which is discharged via the supplied air. This water vapor discharged together with the air may be supplied to the above described sewage water purification as a condensate.

The air flowing off from the reactor 1 is laden with carbon dioxide as a decomposition product and with the water vapor produced by the heating. The exhaust air laden with organic components may be supplied to a biofilter wherein biological cleaning by means of aerobic micro-organisms takes place.

As a leaching fluid initially pure water is used, which is made acidic by salts dissolved during the aerobic treatment following the startup of the installation and obtention of nearly stationary process parameters. The slight acidification of the water enhances leaching of soluble organic, inorganic substances and water-soluble fatty acids.

As is moreover represented in FIG. 1, the mixture of substances 2 located inside the reactor 1 is subjected to intermittent pulses due to the reciprocating movement of the conveyor wedges 46, whereby shear, transversal and longitudinal forces are introduced into the mixture of substances and possibly formed flow channels of the leaching fluid and of the air are destroyed. The magnitude of these forces is designed such as to be capable of destroying these channels and chimneys on the one hand, however not to result in destruction of the layered structure.

Figure 6:
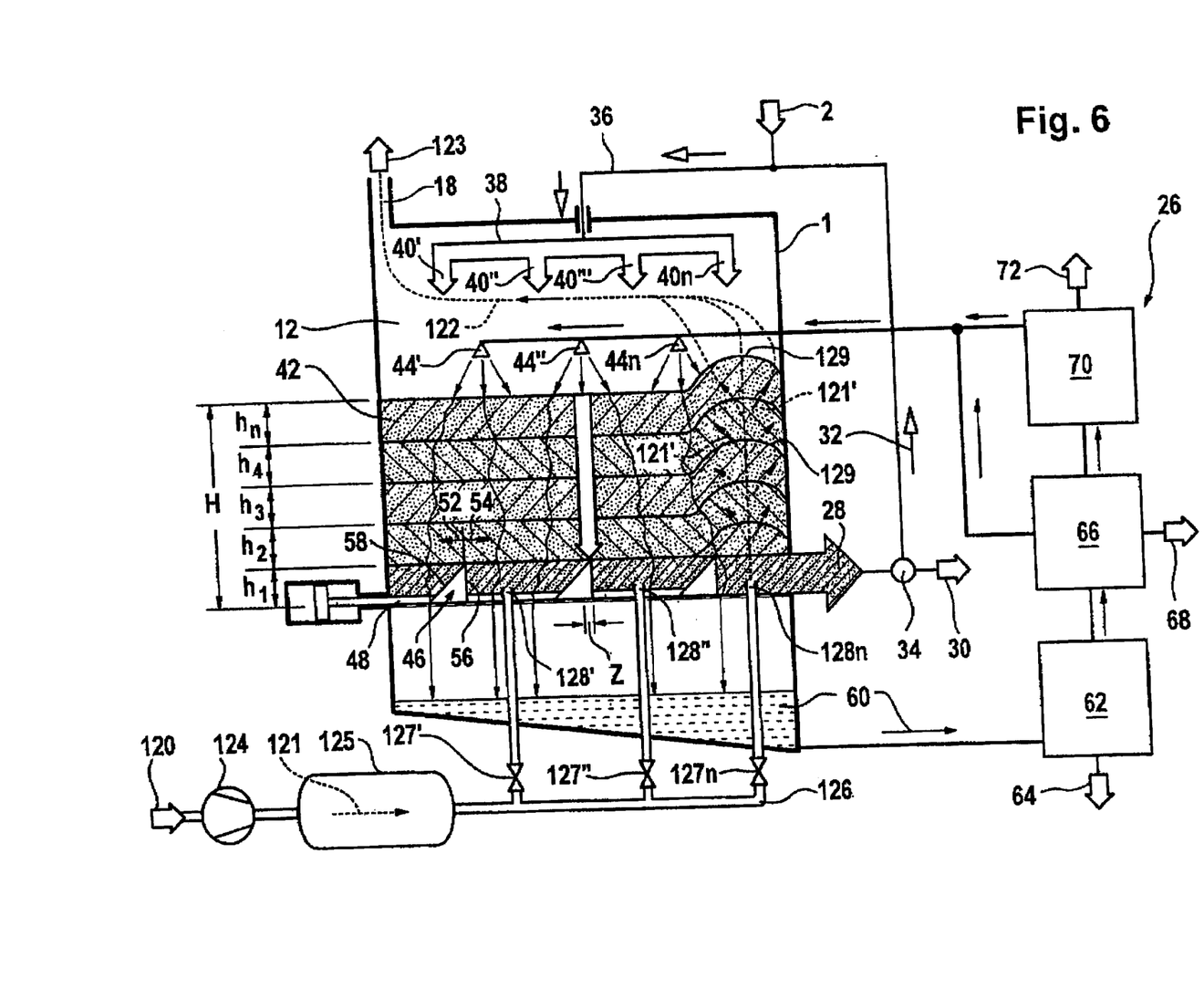
FIGS. 6 and 7 show alternative embodiments of a reactor.
Figure 7:
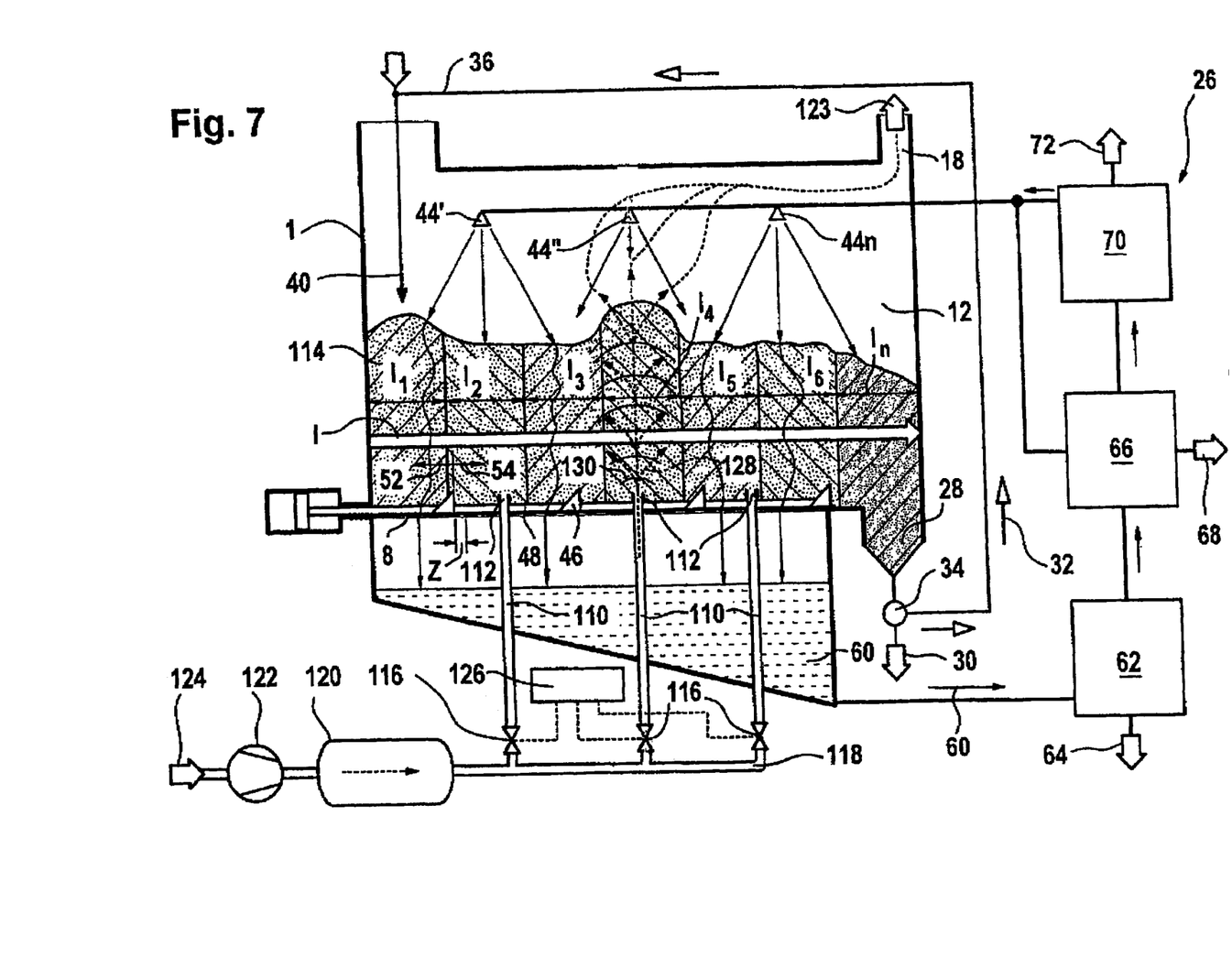

In the embodiment represented in FIG. 1 these pulses are brought about by the movement of the scraper floor; as an alternative, however, as is represented in FIGS. 6 and 7, additional means for inducing shear forces in the mixture of substances 2 and for destroying the Channels might be employed, as represented in FIGS. 6 and 7.

Following the above described hydrolysis, i.e. following decomposition of the organic constituents and extraction of these constituents by means of the leaching fluid, the discharge material 28 is supplied to a drying step. It was found to be particularly advantageous if this drying takes place as aerobic drying, for the residual humidity may then be reduced at minimum energy expense. The like aerobic drying may be effected, for example, by interrupting the supply of leaching fluid through the distributor 20, so that nothing but air flows through the mixture of substances 2 following hydrolysis. As a result of flow through the humid mixture of substances 2, further aerobic decomposition of the as yet available carbon C into carbon dioxide takes place. Moreover, similarly to hydrolysis, the mixture of substances is heated due to the microbial conversion and thereby water vapor is discharged by way of the flow of air passing through. Due to the aerobic decomposition of the carbon and discharge of the water vapor, the residual humidity of the mixture of substances is reduced, with the desired proportion of dry substrate being adjustable in a simple manner through the duration of aerobic drying.

In the above described embodiment, hydrolysis and aerobic drying are thus performed in a single reactor 1. I.e., the reactor 1 may be used both for drying and percolation without any modification, so that a simple structure of the installation is ensued.

Figure 2:
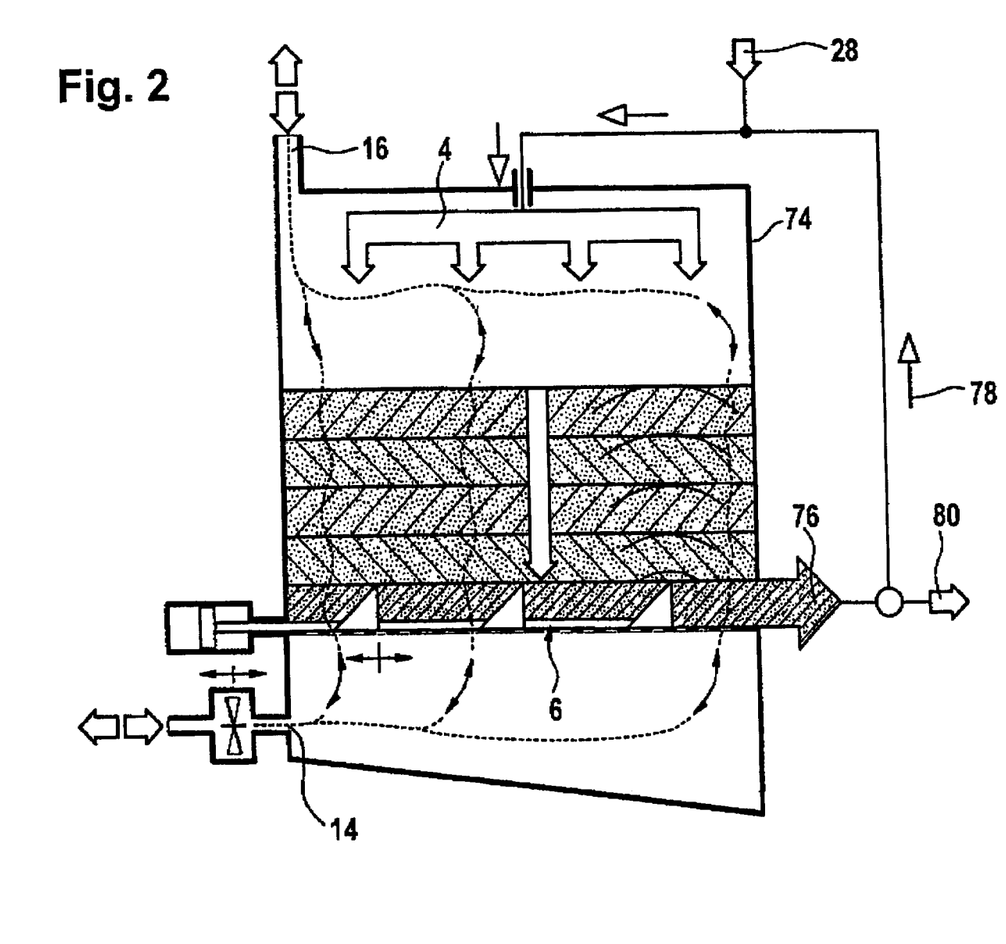
FIG. 2 shows a reactor for performing aerobic, thermophilic drying.

As an alternative, it would be possible to arrange downstream from the reactor 1 of FIG. 1 a dryer in accordance with FIG. 2 to which the discharge material 28 from the reactor 1 is supplied. This aerobic dryer 74 essentially has the same construction as the reactor 1 of FIG. 1, i.e. the mixture of substances, in this case the discharge material 28, is introduced via a charging means 4 into a container provided with lock means, and following completed aerobic drying is discharged via a discharge means 6. Other than the above described reactor 1, the dryer 74 has a plurality of air connection ducts 14 arranged above each other perpendicularly to the plane of drawing, so that the air may be injected in sheet form. The drying air, in turn, may be guided in counterflow or in parallel flow with the flow of the mixture of substances and is accordingly supplied and discharged through air connection ducts 14, 16.

Other than the reactor of FIG. 1, the dryer 74 of FIG. 2 does not include a distributor 20 for the application of leaching fluid.

In the aerobic dryer 74, in turn, partial recirculation of the dry material 76 present at the exit from the dryer 74 as circulation material 78 and/or discharge of a dried product 80 is provided for. The mixture of substances to be dried passes through the dryer 74, once again preferably in a layered form, with channel formation being suppressed by shear, transversal and longitudinal forces applied in the form of pulses. This 2-stage process might, of course, be carried out by means of two reactors arranged in sequence in accordance with FIG. 1, with hydrolysis in the first reactor taking place through supplying air and leaching fluid, whereas in the second, downstream reactor 1 only aerobic drying an a result of supplying air takes place.

Figure 3:
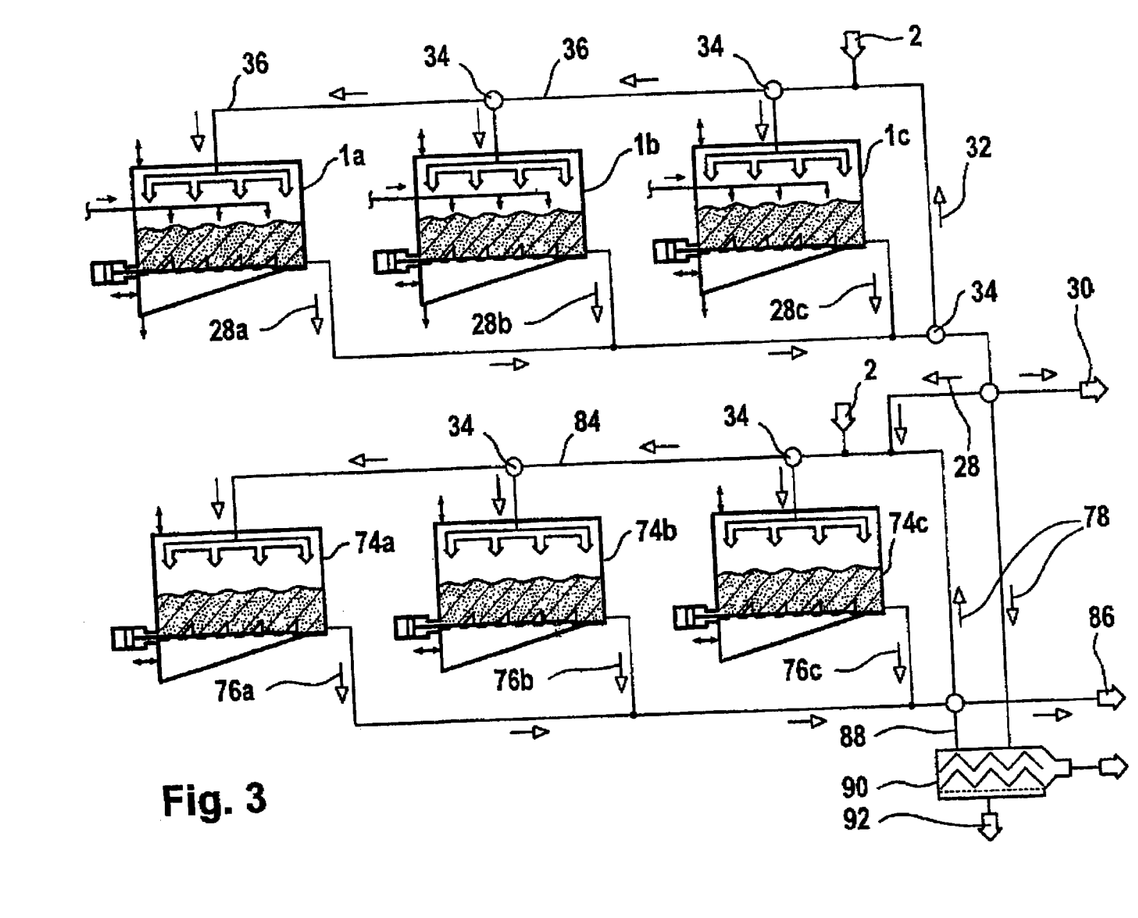
FIG. 3 shows an installation having a plurality of hydrolysis and drying reactors in accordance with FIGS. 1 and 2 arranged in sequence.

FIG. 3 shows an embodiment wherein three reactors 1a, 1b, 1c in accordance with FIG. 1 are combined with three dryers 74a, 74b, 74c in accordance with FIG. 2. Accordingly, a common conveyor means 36 is associated to the three reactors 1a, 1b, 1c, whereby the mixture of substances 2 may be supplied to the single reactors 1a, 1b, 1c. By means of suitable apportioning means 34, in turn, the flow of material to the single reactors 1a, 1b, 1c may be adjusted.

The discharge material 28a, 28b, 28c from the single reactors 1a, 1b, 1c may in turn be recirculated by way of the apportioning means 34 als circulation material 34 or, in turn, supplied as product 30 to further processing, or as discharge material 28 to the aerobic drying. Herein the discharge material 28 from reactors 1a, 1b, 1c is supplied to the dryers 74a, 74b, 74c through conveyor means 84 and suitable apportioning means 34.

In the schematic representation of the installation in accordance with FIG. 3 it is furthermore provided that the mixture of substances 2 is also supplied to drying directly, i.e. while bypassing the reactors 1. This is the case, for example, when the mixture of substances present already includes a considerable proportion of dry substance, so that no more wet washing takes place.

The discharge material from the dryers 74, i.e. the dry material 76a, 76b, 76c is then either further processed as dry product 86, again supplied to drying as circulation material 78, or supplied to means 90 for dewatering and/or compacting as an intermediate product 88.

The means 90 is also used for further processing of the discharge material from the reactors/dryers represented in FIGS. 1, 2. The means 90 may, for example, have the form of an extruder or a dryer/extruder press so that as a result of the mechanical action and the heat generated by the pressure buildup, further dewatering or drying of the intermediate product 88 takes place.

Inside the meats 90 the extracted residual waste is adjusted to a dry substance content of >60%. In a preferred embodiment the means 90 moreover contains a high-performance press whereby the extracted, dewatered material may be pelleted. Herein densities of 1.7 t/m$^3$ are attained. The energy expense for producing the pellets amounts to approx. 1% of the energy content of the pellets when one assumes a mean energy content of 14 MD/kg.

Depending on the design of the means 90, the dewatered final product 92 may be present as a pellet, briquet or in another compacted form. By the above described process steps a product may be produced which cannot be eluted further, has no breathing activity, and is characterized by a large proportion of dry substance, wherein it is not necessary to employ thermal energy from the outside for drying in contrast with the known process.

The material dewatered with the aid of the means 90 may be subjected to subsequent drying by means of composting or belt drying. Conventionally post-rotting was previously connected after a mechanical-biological treatment of waste in order to attain additional decomposition of organic material and drying of the leached residue. Post-rotting may readily take place in an exposed pit. The proportion of biogenic material is sufficiently high even after percolation, so that the rotting temperature will rise to 70° C. within 4 to 6 days. Within 10 to 16 days the residue thus treated attains a dry substance content of up to 80%. As waste heat for drying of the percolation residue would be available in the above described process owing to biogas extraction and conversion into electricity in a gas engine, a space-saving drying process may also be employed for post-rotting.

The arrangement represented in FIG. 3 is selected when a continuous operation is desired. At high throughputs, the installation may be expanded by adding further modules (reactors 1, dryers 74).

The conveying means 36 and 84 and the apportioning means 34 (material deflection) may be controlled such that the order of charging, emptying or mixing (circulation material) of the single reactors, dryers may be changed in any desired order.

Figure 4:
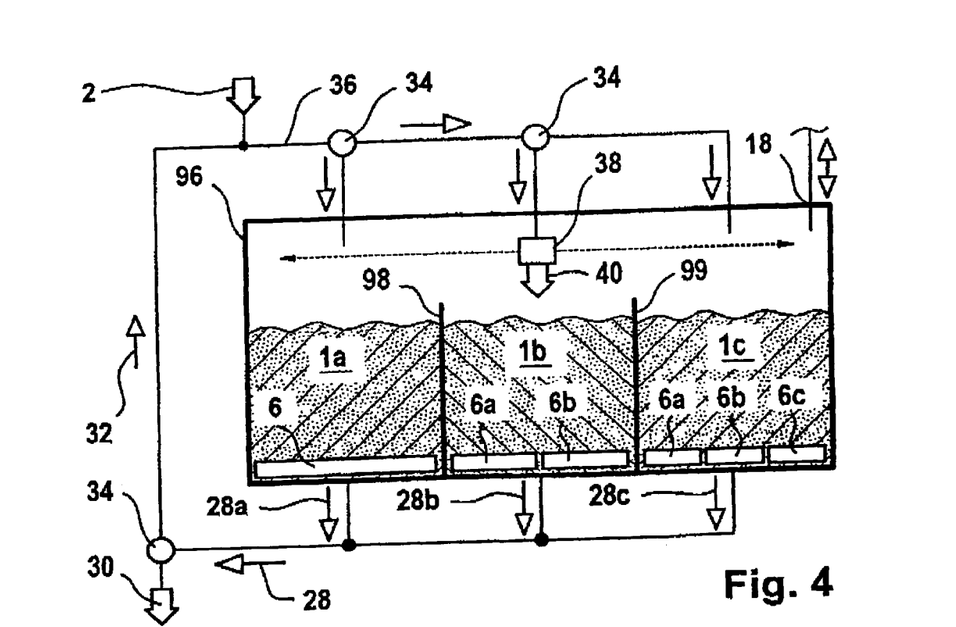
FIG. 4 shows a device having a plurality of reactors for hydrolysis and/or drying arranged in sequence in a commnon container.

FIG. 4 shows an embodiment wherein a container 96 is separated into three chambers or reactors 1a, 1b, 1c by two partition walls. These chambers correspond to the means in accordance with FIG. 1 and in accordance with FIG. 2 wherein the hydrolysis and/or the aerobic drying may be carried out.

To the tight container 96 a common conveyor means 36 is associated whereby the mixture of substances 2 to be processed is supplied to the container 96. By the common conveyor means 36 the mixture of substances is guided via the apportioning means 34 to a transversal conveyor 38 having the form of a distributor crane in the shown embodiment. The latter includes a material chute 40 which is movable across the entire cross-sectional area of the container 96 by means of the distributor crane (transversal conveyor 38). Hereby it is ensured that the partial spaces 1a, 1b, 1c of the container 96 may be charged with the layered mixture of substances 2.

Discharging the treated mixture of substances (discharge material 28 or dry material 76) takes place. through a discharge means 6 which may, for example, be designed like the one in FIG. 1. In accordance with the variants represented in FIG. 4, it is also possible to form a plurality of discharge means 6a, 6b, 6c in laterally adjacent arrangement in the range of the floor of the container 96. In the shown embodiment the container 96 has the form of a multiple-chamber dryer designed to have air connection ducts 14, 18, with only the air connection duct 18 arranged on top being shown in FIG. 4. In this variant, as well, it is provided that the air is guided to the mixture of substances in parallel flow or in counterflow. The container 96 might, of course, also be designed as a reactor having a plurality of partial chambers. The reactors/dryers represented in FIGS. 1 to 3 may, of course, also be designed to include a plurality of laterally adjacent discharge means 6.

The discharge material 28 may be returned to the conveyor means 36 via the apportioning means 34 as circulation material 32, or, however, be discharged as product 30.

Figure 5:
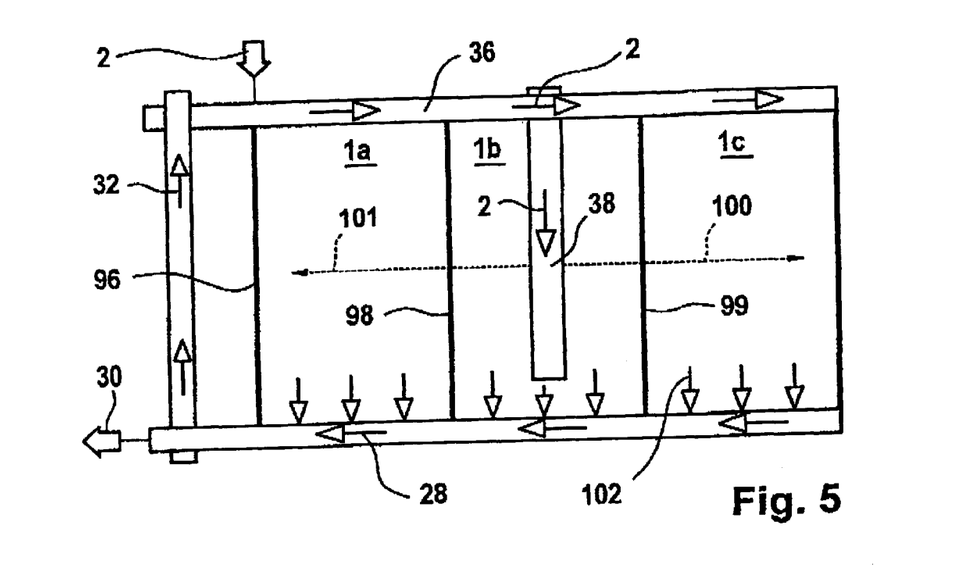
FIG. 5 is a top view of the device of FIG. 4.

FIG. 5 shows a top view of the container 36 of FIG. 4 explaining distribution of the mixture of substances 2. Accordingly, the mixture of substances 2 is charged on the conveyor means 36, for example a conveyor belt, and thereby supplied to a distributor crane 38 that is movable in the direction of arrows 100, 101 above the partition walls 98, 99. The distributor crane 38 carries one movable or a plurality of stationary material chutes 40, so that the entire width (vertical FIG. 5) of the partial chambers 1a, 1b, 1c may be covered.

The processed mixture of substances is discharged from the container 96 in the direction of arrow 102, and this discharge material 28 is carried off through suitable conveyor means either as product 30 or as circulation material 32. The latter is transported back to the conveyor means 36 by a conveyor belt and then once more charged into one of partial spaces 1a, 1b, 1c.

In the above described embodiments, formation of chimneys was prevented by the forces introduced into the bulk material through the discharge means 6, which caused a wave-type vertical displacement in the heap material and thus resulted in reformation of the heap material surfaces and destruction of channels. Depending on the quality of the mixture of substances to be processed, the shear forces thus introduced may, however, sometimes be too weak for bringing about the required mechanical decomposition of the bulk material. In the above described reactors 1 the proportion of the circulation material 32 is then increased, so that the shear forces required for material decomposition are then introduced by way of the conveyor elements for conveying the circulation material 32.

With respect to energy and material expenditure, this variant is still substantially more favorable than the prior art described at the outset, wherein agitators are used inside the reactor in order to introduce the shear forces.

The expenditure in terms of energy and apparatus technology may be further reduced if the reactor/dryer according to the invention is designed in the manner described in FIGS. 6 or 7.

In the embodiments described in FIGS. 1 and 2, the process air was injected into the bottom portion of the reactor 1 or dryer, respectively, through one or a plurality of air connection ducts 14 and then enters through the sieve floor 8 into the heap material (bulk material). In contrast, in the embodiments represented in FIGS. 6 and 7, the process air is injected through a multiplicity of lances 110 distributed over the crosssection of the reactor 1, the nozzles 112 of which open into the lower range (view of FIGS. 6, 7) of the bulk material 114. The lances 110 extend through the sieve floor 8 and the discharge means 6—in the present case the sliding floor.

The lances 110 for process air or pressurized air are each connected through a control valve 116 to a pressure line 118 which opens into a pressure accumulator 120. The latter is connected to a compressor 122 through which fresh air or air 124 recycled from the exhaust air treatment (biofilter) may be taken to the system pressure, i.e. the pressure in the pressure accumulator 120. The control valves 116 are connected to a process control means 126 and may thus individually be controlled open and closed, respectively.

The opening cross-section of the control valves 116 may be continuously variable depending on the process control means 126, so that the pressure of the process/pressure gas is variable.

The system pressure in the pressure accumulator 120 is preferably adjusted to a pressure of more than 4 bar. Upon complete opening of a control valve 116 of a lance 110, pressurized air 128 exits from the nozzle opening in an upwardly direction (view of FIGS. 6, 7) and flows through the bulk material 114 in a vertical direction at the maximum pressure, with the arrows in FIGS. 6, 7 indicating that the pressurized air 128 is also deflected in the transversal direction. The bulk material 114 is partially whirled up or fluidized in the range through which the pressurized air 128 flows, so that the surfaces of the heap material are reformed and channels are destroyed. I.e., by the injected pressurized air a partial undulating movement 130 is generated in the bulk material 114, which moves away from the nozzle 112 of the respective lance 110 through the bulk material 114 in an upwardly direction. Due to this undulating movement, a relative movement of the mixture of substances is induced, so that the surfaces of the particles are torn open and thus the mass transfer area is increased. As the pressurized air is only injected in pulses, the bulk material 114 again collapses after the control valves 116 are closed, no that again shear forces are introduced into the bulk material 114 which result in repeated reformation of the surfaces and in destruction of channels. The laden air 123 exiting from the reactor 1 is supplied to a biofilter.

Owing to the injected pressurized air, basically two effects are attained. For one thing shear forces are introduced in the above described manner into the bulk material 114, on the other hand the process air required for hydrolysis and/or drying is also supplied, so that the introduction of shear forces and feeding of process air are practically combined. Model calculations have shown that on account of the pressurized air connection duct according to the invention, the energy requirement may be reduced by up to in excess of 50% in comparison with a conventional reactor including an agitator.

The process control 126 and the control valves 116 are designed such that the pressure of the process/pressurized air may be varied over time, so that for example over a predetermined time interval process air only having a low pressure (0.5 bar) is supplied which is required for drying or hydrolysis, however does not result in considerable introduction of shear forces into the bulk material 114. Depending on the bulk height and the quality of the mixture of substances to be processed, pressurized air is then intermittingly supplied at a comparatively high pressure (>4 bar) in order to introduce the above described shear forces and avoid a formation of channels.

The valves 116 of the multiplicity of pressure lances 110 of the reactor 1 may also be controlled consecutively, so that an "expansion wave" propagating in parallel with the plane of drawing or perpendicularly to the plane of drawing in the representation according to FIGS. 6 and 7 passes through the bulk material.

For the rest, the embodiment represented in FIG. 6 corresponds to the above described embodiments. I.e., the mixture of substances 2 is introduced into the reactor 1 by way of the charging means 4 from above in a layered configuration and migrates through the latter, with the layered structure remaining substantially unchanged due to the supply of pressurized air and the resulting partial fluidization of the bulk material. The processed mixture of substances is then discharged via the discharge means 6, i.e. a sliding floor, and supplied to the further treatment steps.

In the embodiment represented in FIG. 7, the mixture of substances 2 is supplied at the left-hand front face of the reactor 1 in the representation of FIG. 7 and is at the opposite side of the reactor 1 discharged in a downwardly direction. Accordingly, the mixture of substances migrates through the reaction chamber 12 having a vertically arranged layered structure as is designated by reference symbols $l_l$ to $l_n$. I.e., the mixture of substances moves through the reactor in a horizontal direction (l) while being displaced through the reactor in a vertical direction in the embodiment represented in FIG. 6.

For the rest, the embodiments represented in FIGS. 6 and 7 correspond to the above described embodiments, so that reference is made to the above explanations with regard to the remaining components. For the sake of simplicity, the same reference numerals were used in FIGS. 6 and 7 for corresponding components as in FIGS. 1 to 5.

In simple words, in the embodiments represented in FIGS. 6 and 7 the agitator used in the prior art was replaced with a "pressurized air agitator", with the pressure for the pressurized air being selected such that the layered structure is essentially preserved. Thanks to the possibility of individually controlling the control valves 116 that are distributed over the cross-section of the reactor 1, the bulk material 114 may purposely be subjected to pressure pulses, so that the introduction of shear forces may be applied depending on the process, i.e., application of pressurized air bzw. process air may be effected as a function of the quality of the mixture of substances to be processed and of the dwell time in the reactor 1. The applicant reserves the right of directing independent sets of claims to the variants represented in FIGS. 6 and 7 and 1 to 5.

A process for treating a mixture of substances containing structured constituents and organic matter, and a device for carrying out this process are disclosed. In accordance with the invention, the mixture of substances is subjected to pulse-type or periodical application of force, so that the formation of flow channels for a leaching fluid or process air in a bulk material may be prevented.

What is claimed is:

1. A process for treating a mixture of substances containing structured constituents and organic matter which is received in the form of bulk material and subjected to aerobic decomposition or aerobic drying in a reactor by means of a flow of process air therethrough and/or addition of a leaching fluid so that the soluble organic constituents are discharged, characterized in that said mixture of substances is subjected to pulse-type or periodical application of pressurized air having a pressure of more than 2 bar and directed approximately perpendicular to and/or in parallel with a direction of displacement of said mixture of substances so as to introduce shear forces and prevent channel formation, and in that at least a part of a discharged material is recirculated into the reactor as circulation material for inoculating the mixture of substances and for accelerating the biological decomposition, wherein the mixture of substance is moved towards a discharge opening by a discharge means arranged at a bottom portion of the reactor, and when the discharge means moves away from the discharge opening, the discharge means introduces forces into the bulk material.

2. The process according to claim 1, wherein the pressurized air or process air, respectively, is supplied through nozzles in a head portion and/or in a bottom portion of said reactor.

3. The process according to claim 2, wherein the process air and the pressurized air are supplied through said same nozzles.

4. The process according to claim 3, wherein said mixture of substances subsequently passes through a plurality of decomposition and/or drying steps.

5. The process according to claim 2, wherein the process air is sucked through the mixture of substance.

6. The process according to claim 1, wherein said reactor is operated continuously, and the mixture of substances is guided through said reactor approximately in parallel with or transversally to the process air.

7. The process according to claim 1, wherein the leaching fluid is supplied through a distributor in a head portion of said reactor.

8. The process according to claim 1, wherein said aerobic decomposition is followed by am aerobic drying of said mixture of substances.

9. The process according to claim 1, wherein said decomposition and/or aerobic drying is followed by compacting of the mixture of substances.

10. The process according to claim 1, wherein at least a part of the dry material is again supplied into a dryer for drying as circulation material.

11. A device, including a reactor having associated a charging means for introduction of a mixture of substances, wherein inlets for introducing process air are arranged in a bottom portion and/or in a head portion of said reactor and/or a distributor for leaching fluid is arranged in the head portion of said reactor, characterized by a pressurized air system via which pressurized air of more than 2 bar may be supplied in the form of pulses or periodically for decomposition of said bulk material, and by means for recirculating into the reactor at least a part of a discharged material as circulation material for inoculating the mixture of substances and for accelerating the biological decomposition, the discharged material is moved towards a discharge opening by a discharge means arranged at a bottom portion of the reactor, and when the discharge means moves away from the discharge opening, the discharge means introduces forges into the bulk material.

12. The device according to claim 11, wherein said pressurized air system includes nozzles opening in the bottom portion of said reactor and connected to a pressure accumulator fed by a compressor.

13. The device according to claim 12, wherein air conveying means are arranged for sucking the process air through the mixture of substance.

14. The device according to claim 11, wherein said pressurized air system is associated with a control means through which the pressure of pressurized air or process air may be varied.

15. The device according to claim 11, wherein said pressurized air and process air may be supplied jointly through said pressurized air system.

16. The device according to claim 11, further comprising a gas purification system for purification and recirculation of the process air and/or pressurized air.

17. The device according to claim 11, wherein excitation means is at least partly constituted by the discharge means at the bottom portion of said reactor.

18. The device according to claim 11, wherein a plurality of reactors ate arranged in series, with several reactors arranged in parallel having associated a commnon charging means whereby said mixture of substances to be treated may be supplied.

19. The device according to claim 11, further comprising a compacting means for compacting, dewatering and shaping said mixture of substances which have been treated.

20. The device according to claim 11, wherein at least one dryer is provided for drying the discharged material discharged from the reactor, whereby the at least one dryer includes means for recirculating into the dryer at least a part of the dry material as circulation material.

* * * * *